United States Patent [19]

Tamagnone et al.

[11] 4,029,811
[45] June 14, 1977

[54] CERTAIN ANTIINFLAMMATORY DIHYDROBENZOFURAN AND DIHYDRONAPHTHOFURAN ACETIC ACID COMPOUNDS

[75] Inventors: Gian Franco Tamagnone; Franco De Marchi, both of Turin, Italy

[73] Assignee: SCHIAPPARELLI - Stabilimenti Chimici Farmaceutici Riuniti S.p.A., Turin, Italy

[22] Filed: June 9, 1975

[21] Appl. No.: 585,408

[30] Foreign Application Priority Data

June 12, 1974 United Kingdom ............ 26078/74

[52] U.S. Cl. ..................... 424/285; 260/346.2 R; 260/346.2 M
[51] Int. Cl.² ..................... A61K 31/34
[58] Field of Search ............ 260/346.2 R, 346.2 M; 424/285

[56] References Cited

UNITED STATES PATENTS 3,452,085  6/1969  Lauria et al. ............... 260/346.2 R

*Primary Examiner*—Henry R. Jiles
*Attorney, Agent, or Firm*—Stevens, Davis, Miller & Mosher

[57] ABSTRACT

Compounds of the general formula

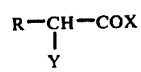

wherein R represents a group selected from:

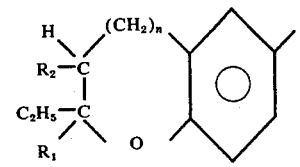

and

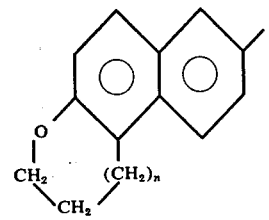

where:
$n = 0,1$;
$X = OH, OCH_3, OC_2H_5$;
$Y = H, CH_3$;
$R_1, R_2$, that may be the same or different $= H, CH_3, C_2H_5, C_3H_7$; and their water soluble pharmaceutically acceptable salts.

The compounds are prepared by introducing the acidic moiety upon the heterocyclic nuclei which can be prepared according to known procedure.

The present invention relates to novel antiinflammatory agents and specifically to certain novel heterocyclo alkanoic acids. More particularly it relates to heterocyclo-acetic and to 2-(heterocyclo)propionic acids in which the heterocyclo moiety of the molecule is an oxygen containing nucleus.

7 Claims, 1 Drawing Figure

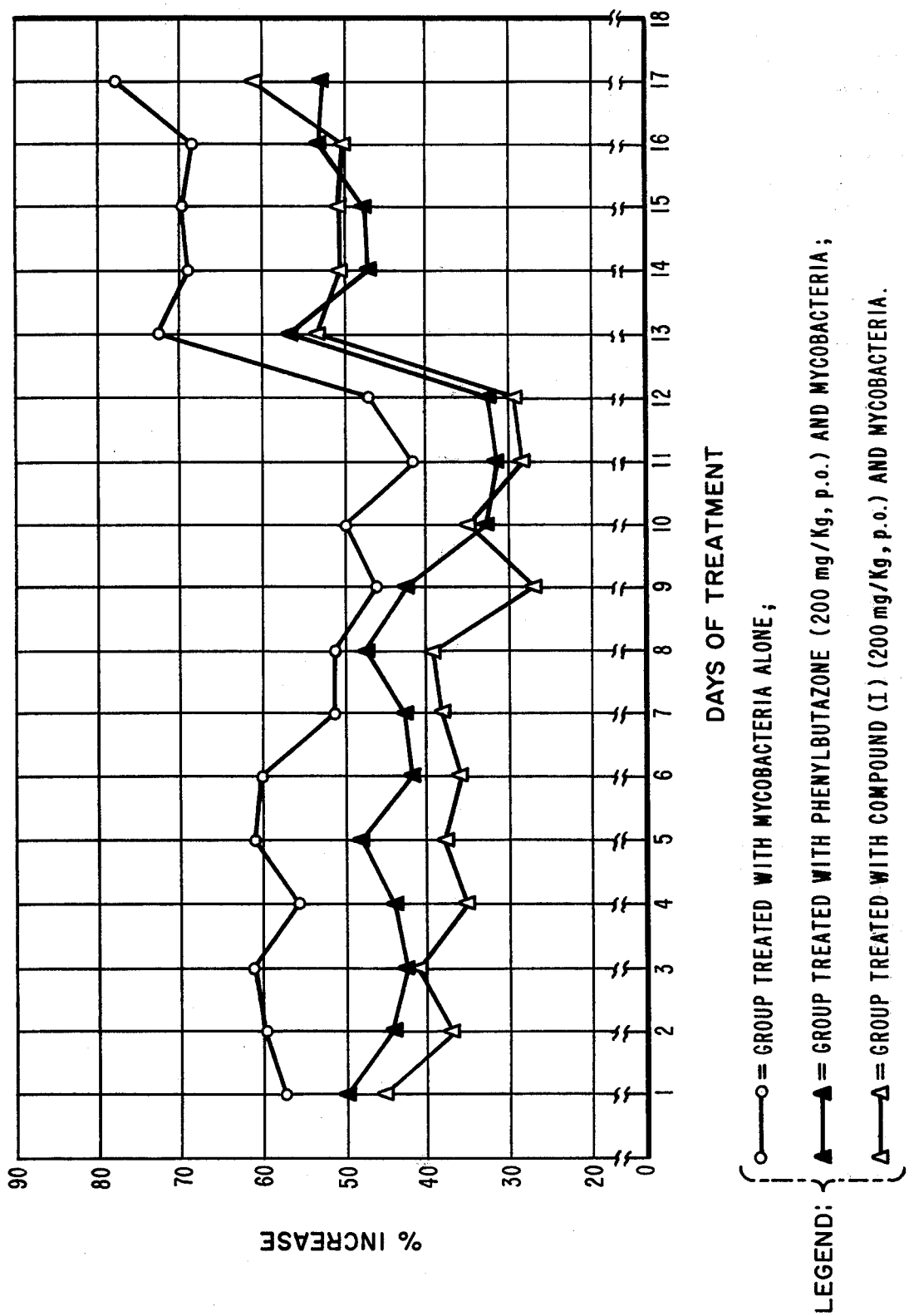

CERTAIN ANTIINFLAMMATORY DIHYDROBENZOFURAN AND DIHYDRONAPHTHOFURAN ACETIC ACID COMPOUNDS

This invention relates to new compounds having improved antiinflammatory activity corresponding to the following structural formula

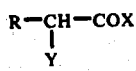

wherein R represents a group selected from:

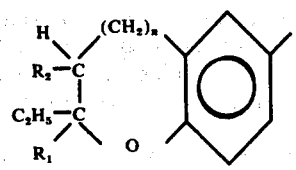

and

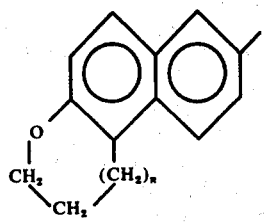

where:
n = 0,1;
X = OH, OCH$_3$, OC$_2$H$_5$;
Y = H, CH$_3$;
R$_1$, R$_2$ that may be the same or different = H, CH$_3$, C$_2$H$_5$, C$_3$H$_7$; and their water soluble pharmaceutically acceptable salts.

Broadly defined the compounds of the present invention are therefore: dihydra derivatives of benzofuranyl-, benzopyranyl-, naphthofuranyl-, naphthopyranyl- acetic or -2-propionic acids and the salts and the esters of the above mentioned acids.

Examples of compounds according to the invention are: 2,3-dihydro-2-ethyl-benzofuran-5-yl-acetic acid; 2-ethylchroman-6-yl-acetic acid; 1,2-dihydronaphtho [2,1-b]furan-7-yl acetic acid; IH-2,3-dihydra naphtho [2,1-b]pyran-8-yl-acetic acid; the corresponding heterocyclo-2-propionic acids and the esters and salts of the above mentioned acids.

It has been found that the compounds of the present invention possess important antiinflammatory properties and a low toxicity, which makes them particularly valuable for use as antiinflammatory agents.

These compounds are also well tolerated upon prolonged administration at high doses and possess also antipyretic and analgesic activity.

The compounds were synthesized by introducing the acidic moiety upon the heterocyclic nuclei, which were prepared according to the known procedures. The following procedures can be followed for the synthesis of the heterocyclo- substituted acetic acids:

1,a. acetylation of the parent heterocyclic ring with acetic anhydride and aluminum chloride in nitrobenzene, subsequent treatment of the resulting ketone with sulphur and morpholine under reflux and hydrolysis of the intermediate aceto-thiomorpholide derivative with aqueous sodium hydroxide;

1,b. acetylation of the parent heterocyclic ring with ethyl-chloroglyoxylate (C$_2$H$_5$OCOCOCl) and aluminium chloride in nitrobenzene to give the substitutedglyoxylic acid ethyl ester; hydrolysis of this ester to the corresponding keto-acid with sodium hydroxide in hydro-alcoholic solution; reduction of the acid with hydrazine hydrate in ethylene glycol;

1,c. chlormethylation of the parent heterocyclic ring with formaldeyde and HCl; treatment with an alkali metal cyanide to obtain the corresponding cyanide and subsequent hydrolysis to acid.

The following procedures can be followed for the synthesis of the heterocyclo-substituted-2-propionic acids of the present invention:

2,a. acetylation of the parent heterocyclic ring with ethyl-chloroglyoxylate and aluminium chloride to give the substituted glyoxylic acid ethylester, hydrolysis to the corresponding glyoxylic acid with sodium hydroxide, reaction with methyl magnesium halide in dry ether to give the -2(2-hydroxy)-propionic acid; dehydration of this compound in the presence of an acid to (α-methylene)-acetic acid and catalytic hydrogenation of this compound;

2,b. methylation of the ethyl ester of the corresponding heterocyclo-substituted acetic acid with methyl iodide and subsequent hydrolysis;

2,c. chloromethylation of the heterocyclic ring with formaldehyde and HCl; treatment with alkali cyanide to obtain the nitrile; methylation of the nitrile with methyl iodide and final hydrolysis;

2,d. reaction of the ethyl ester of the heterocyclo-substituted-acetic acid with diethylcarbonate and sodium ethoxide (preferably in the presence of a solvent boiling above 100° C) to give the heterocyclo-substituted-malonic acid diethylester; methylation of the above compound with methyl iodide to the corresponding (α-methyl)-malonic acid derivative; hydrolysis to the corresponding diacid and subsequent decarboxylation by heating at temperatures above 80° C;

2e. chloroethylation of the parent heterocyclic ring with acetaldehyde and HCl; treatment with alkali cyanide to obtain the corresponding nitrile and final hydrolysis;

2,f. acetylation of the parent heterocyclic ring with acetic anhydride and aluminium chloride, treatment with alkali cyanide to obtain the corresponding cyanohydrine; dehydration of the cyanohydrine in the presence of an acid, hydrolysis to carboxylic acid and final hydrogenation.

The salts of the acids according to the present invention can be obtained by reaction of the acids with the corresponding bases. The preferred salts are the alkali metal salts, particularly the sodium salt. As organic bases salts, there are particularly preferred those derived from triethanolamine, N-methyl-glucamine and arginine.

The new esters of the present invention, when not obtained as intermediate products in the processes given above, can be obtained by esterification under usual conditions of the heterocyclo-substituted acetic and propionic acids with the corresponding alcohols.

The following examples are given to illustrate the new compounds of the present invention as well as their preparation processes.

EXAMPLE I

Synthesis of 2,3-dihydro-2-ethylbenzofuran-5-yl-acetic acid —(Compound I) according to procedure 1,a.

A solution of 2,3-dihydro-2-ethylbenzofuran (148.2 g; 1.0 moles) in acetic anhydride (112.3g; 1.1 moles) was slowly added under stirring to a cold solution of $AlCl_3$ (266.7 g; 2.0 moles) in nitrobenzene (1100 ml).

After stirring overnight at room temperature, the mixture was treated with ice (200 g) and concentrated HCl (200 ml). After steam distillation of the nitrobenzene, the oil residue was taken up in ethyl ether.

The solution was washed with water, dried ($MgSO_4$) and the residue obtained after evaporation of solvent was distilled under reduced pressure yielding 150.0 g (79%) of 2,3-dihydro-2-ethyl-5-acetylbenzofuran as a colorless oil, b.p. 118°–20° C (0.3 mmHg).

A mixture of 2,3-dihydro-2-ethyl-5-acetylbenzofuran (177.0 g; 0.93 moles), sulphur (48.2 g; 1.5 moles) and morpholine (130.7 g; 1.5 moles) was refluxed for 16 hours. The residue was triturated with ethanol and the crude 2,3-dihdro-2-ethylbenzofuran-5-acetylthiomorpholide thus obtained was refluxed with 2 N NaOH (1400 ml; 2.8 moles) for 6 hours.

The clear solution was washed with methylene chloride and acidified with 5 N HCl. The solid which separated was collected, dried and crystallized from carbon tetrachloride (300 ml). Recrystallization from cyclohexane (2800 ml) gave 80.0 g (42%) of compound (I), white crystals, m.p. 94°–95° C.

Analysis: Found % : C, 70.07; H 6.72.
Calculated for $C_{12}H_{14}O_3$ : C, 69.88; H, 6.84.
Title (0.1 N KOH in EtOH/DMF): 100 ± 1%

The compound had proper N.M.R. and I.R. spectra and moved as a single spot of T.L.C. (Solvent system: benzene - dioxane - acetic acid (100 : 10 : 4); $Rf = 0.6$ (silicagel).

EXAMPLE II

Synthesis of 2-ethylchroman-6-yl-acetic acid —(Compound II)

Starting from 2-ethylchroman and operating according to the procedure of Example I, the title compound was obtained, m.p. 88°–90° C (cyclohexane); analysis: Found % : C, 70.96; H, 7.41; calculated for $C_{13}H_{16}O_3$: C, 70.89; H, 7.32.

EXAMPLE III

Synthesis of 1,2-Dihydronaphtho [2,1-b] furan-7-acetic acid — (Compound III).

Starting from 1,2-dihydrohapto [2,1-b]furan and operating according to the procedure of Example I the title compound was obtained, m.p. 181°–3° C (benzene); analysis: found % : C, 73.83; H 5.19; calculated for $C_{14}H_{12}O_3$: C, 73.67; H, 5.30.

EXAMPLE IV

Synthesis of 1H-2,3-Dihydronaphtho [2,1-b]pyran-8-yl-acetic acid — (Compound IV)

Starting from IH- 2,3-dihydroanaphtho [2,1-b] pyran and operating according to the procedure of Example I, the title compound was obtained, m.p. 165°–6° C (toluene); analysis: found % : C, 74.43; H, 5.79; calculated for $C_{15}H_{14}O_3$: C, 74.36; H, 5.83.

EXAMPLE V

Synthesis of 2(1H-2,3-dihydronaphtho [2,1-b]pyran-8-yl-propionic acid — (Compound V) according to procedure 2,d.

Preparation of 1H-2,3-Dihydronaphtho [2,1-b]pyran-8-malonic acid diethylester.

A solution of 2N ethanolic sodium ethoxide (300 ml) was added dropwise at 100° C to a mixture of diethylcarbonate (355g; 3.0mol) and 1H-2,3-dihydronaphtho [2,1-b]pyran-8-yl-acetic acid ethyl ester (134 g; 0.5 mol. This ester was prepared by refluxing a 10% solution of the corresponding acid in dry ethanol containing 1% sulphuric acid in a Soxlet apparatus, using molecular sieves to remove water). The distilling ethanol was removed and the temperature gradually increased to 120° C. Toluene was added and the heating continued until pure toluene distilled (overall heating time: 6 hours).

The reaction mixture was treated with water and ethylacetate, the organic phase being washed and dried. The residue obtained after evaporation of the ethylacetate was taken up in benzene (1500 ml) and the solution was filtered trough a column of Silicagel Merck 60 (200 g; $20 \times 21$ $cm^2$).

Evaporation of the solvent left a solid residue which was recrystallized from methylene chloride-hexane to give the title compound, m.p. 61°–2° C.

Preparation of 1H-2,3-Dihydronaphtho ]2,1-b]pyran-8-yl-($\alpha$-methyl-)malonic acid diethylester.

To a solution of the above compound (68.5 g; 0.2 mol) in diemthylformamide (200 ml) was slowly added 50% sodium hydride (9.6 g; 0.2 mol). Methyl iodide (35.5 g; 0.25 mol) was added to the clear solution and the mixture was heated at 50° C for 3 hours. The suspension was treated with iced water and methylene chloride.

Removal of the solvent, after washing and and drying, left a residue which was recrystallized from cyclohexane to give the title compound, m.p. 58°–60° C.

Preparation of 2(1H 2,3-Dihydronaptho [2,1-b]pyran-8-yl-propionic acid.

A suspension of the above compound (35.4 g, 0.1 mol) in 1 N NaOH (300 ml) and ethanol (100 ml) was heated at 80° C for 2 hours. The clear solution was washed with ether, acidified (5 N HCl) and extracted with ether.

The extract was washed, dried and the solvent removed.

The decarboxylation was carried out by refluxing for 3 hours in chlorobenzene. Crystallization of the residue obtained after removal of chlorobenzene gave the title compound, m.p. 162°–4° C. Analysis: found % : C, 75.09; H, 6.36; calculated for $C_{16}H_{16}O_3$: C,74.98; H, 6.29.

EXAMPLE VI

Synthesis of 2(2-Ethyl-2,3-dihydrobenzofuran-5-yl)-propionic acid —(Compound VI)

Starting from 2-ethyl-2,3-dihydrobenzofuran-5-yl-acetic acid ethyl ester and following the procedure of Example V, the title compound was obtained, m.p. 70°–72° C (hexane); analysis: found % : C,70.89; H, 7.42; calculated for $C_{13}H_{16}O_3$: C, 70.89; H, 7.32.

Example VII

Synthesis of 2(2-Ethylchroman-6-yl)-propionic acid — (Compound VII)

Starting from 2-ethylchroman-6-yl-acetic acid ethyl ester and following the procedure of Example V, the title compound was obtained, p.m. 66°–7° C (hexane); analysis: found % : C, 71,88; H, 7.90; calculated for $C_4H_{18}O_3$: C, 71.77; H, 7.74.

The compounds of the present invention are particularly suited for solid oral (compresses, capsules, pills) and rectal (suppositories) administration; nevertheless they may be compounded also for liquid, oral (syrups) and parenteral administration. The unit dosage is usually comprised in the range from 25 mg to 250 mg per compress, capsule, pill; and from 50 to 500 mg per suppository. Lower dosages may be employed for pediatric use. The excipients and other vehicles for use with the compounds of the present invention in their pharmaceutical preparations are evident to those skilled in the art. Mycrocristalline cellulose, starch, colloidal silica and magnesium stearate may be cited as excipients for solid forms. Mixtures consisting of triglycerides of saturated vegetable fatty acids, white wax, cocoa butter, macrogels are suitable bases for suppositories.

Typical formulations of compound (I) in capsules and suppositories are given hereunder.

| Capsules: | | |
|---|---|---|
| Compound (I) | mg | 100.0 |
| Microcrystalline cellulose | mg | 46.5 |
| Starch | mg | 1.5 |
| Colloidal silica | mg | 1.0 |
| Magnesium stearate | mg | 0.2 |
| Suppositories: | | |
| Compound (I) | g | 0.25 |
| Base of triglycerides of saturated vegetable fatty acid (with a chain length of $C_{12}$ to $C_{18}$) | g | 2.50 |

TOXICOLOGY

ACUTE TOXICITY

The acute toxicity of compounds of the present invention was investigated in male albino Swiss mice and in male Wistar rats per os using 10 animals for each tested dose (250, 500, 1000 and 1500 mg/Kg, the last one in the rat only). The observations were carried out during 120 hours. The obtained $LD_{50}$ values are shown in Table 1, and compared with those of phenylbutazone, a known antiinflammatory agent selected as reference drug.

Table 1

| Animal | Compound | $LD_{50}$ mg/Kg |
|---|---|---|
| Mouse | (I) | 1000 |
| | (II) | 1000 |
| | (III) | 1000 |
| | Phenylbutazone | 980 |
| Rat | (I) | 1500 |
| | (IV) | 1500 |
| | Phenylbutazone | 690 |

The compounds of the present invention are therefore significantly less toxic than the reference drug, both in mice and in rats.

LONG-TERM TOXICITY

Compound (I) has been tested y employing 40 Wistar rates subdivided into 2 groups of 20 animals (10 male and 10 female). One of the groups (reference group) was fed in conventional manner, while 60 mg/kg daily of the compound on test were administered orally to the animals of the other group. The treatment was continued during 60 days: every 15 days the following aspects were checked: body weight, blood pressure (by incruent method), cardiac frequency, hemochromocytometric examination and urine analysis. No lethal cases have been observed. The food consumption was regular.

No differences have been noted both in body weight increase and in respect of the aspects listed above. At the end of treatment, all animals have been sacrificed and subjected to further examinations (hemochromocytometric, serum-biochemical, enzymatic, electrolytic and autopsic examination).

No significant variations have been observed. It may be concluded that a prolonged administration of compound (I) does not induce biologically relevant alterations.

TERATOGENIC STUDIES

Tests in the attempt of discovering any teratogenic and fetal-toxicity effects have been carried out in conventional manner on Wistar rats, to which compound (I) has been administered orally at dosages of 30 mg/Kg and 60mg/Kg. No. pregnancy disturbances and/or toxic effects on fetus have been observed.

PHARMACOLOGY

Antiinflammatory and analgesic properties of compounds of the present invention have been investigated in mice and rats by various techniques generally adopted to evaluate nonsteroidal antiinflammatory agents.

CARRAGEENIN-INDUCED EDEMA ASSAY

Activity was determined in this test by inhibition of rat hind paw edema induced by subplantar injection of carrageenin (0.1 ml of 1% suspension). The tested compounds, as sodium salts, have been administered orally 1 hour before injection of the irritant.

Paw edema was measured by fluid displacement when the paw was immersed in a cup of mercury. Results were expressed as % inhibition compared to control at 3 hours after injection of carrageenin; they are shown in Table 2 together with those of phenylbutazone and 2-(4-isobutyl-phenyl)-propionic acid-sodium salt (ibuprofen), used as the standards.

Table 2

| Compound | Dose mg/Kg/os | % Inhibition |
|---|---|---|
| (I) | 10 | 28 |
| | 30 | 46 |
| | 90 | 58 |
| | 200 | 68 |
| (II) | 200 | 31 |
| (III) | 200 | 51 |
| (IV) | 200 | 64 |
| (VI) | 12.5 | 19.3 |
| | 25 | 41.6 |
| | 50 | 43.9 |
| | 100 | 59.1 |
| (VII) | 12.5 | 28.7 |
| | 25 | 50.2 |
| | 50 | 31.2 |
| | 100 | 45.9 |
| Phenylbutazone | 10 | 8 |
| | 30 | 17 |
| | 90 | 20 |
| | 200 | 42 |
| Ibuprofen | 12.5 | 42.1 |

Table 2-continued

| Compound | Dose mg/Kg/os | % Inhibition |
|---|---|---|
|  | 25 | 38.1 |
|  | 50 | 52.1 |
|  | 100 | 46.9 |

From these results, the compounds of the present invention appear to be superior to phenylbutazone and ibuprofen as antiinflammatory agent.

EXPERIMENTAL POLYARTHRITIS ASSAY

Three groups of 10 Wistar rats were used. Two groups were treated, respectively, with compound (I) or phenylbutazone (200 mg/Kg, p.o.) 24 hours before subcutaneous injection (left paw subplantar area) of 0.1 ml 0.25% suspension of mycobacteria in paraffin oil (modified Freund's adjuvant) to produce experimental polyarthritis. Pharmacological treatment was carried out for 14 day, while the third group served as control. Paw edema was measured as for the carrageenin-induced edema. Results are reported in FIG. 1 as % increase of paw volume immediately before modified Freund's adjuvant injection. It may be concluded that both compound (I) and phenylbutazone show a significant activity in the experimental polyarthritis assay; (I) seems to be superior to the reference drug, at least in the first 9 days of treatment.

The activity of compound (III) in the experimental poly arthritis assay in the conditions referred above was quite analogous to the activity of compound (I).

ANTI-WRITHING ASSAY

Male albino Swiss Mice, each weighting 20 to 22 g, were used. The animals were fasted for 18 hours before pharmacological treatment. Twenty minutes after administration of the compounds of the present invention and phenylbutazone (200 mg/Kg, p.o.), 0.25 ml per animal of 3% acetic acid was injected intraperitoneally. The number of abdominal stretching was counted for 20 minutes following the acetic acid injection. The % stretching decreases from the control mice are reported in Table 3.

Table 3

| Compound | % Stretching decrease from the control |
|---|---|
| (I) | 81 |
| (II) | 42 |
| (III) | 73 |
| (IV) | 62 |
| Phenylbutazone | 43 |

From these results, the compounds of the present invention appear to be superior to phenylbutazone as analgesic agent.

CLINICAL TESTS

Compound (I) was administered orally to 25 patients 45 to 82 years in age, exhibiting painful osteoarticular processes (coxo and gono arthrosis, lumbosciatalgia, cervicalgia, scapulo-humeral, periarthritis, ecc.).

Fourteen patients were treated with a dosage of 100 mg three times daily, during a period of 3 days; in further seven cases the treatment was 200—300 mg daily during 8-10 days. The remaining four patients received a dosage of 200 mg three times daily during periods of 3 to 5 days.

A significant antalgic-antiinflammatory effect was ascertained upon administration of compound (I): on the whole it was judged good or very good in 17 cases (68%), slight in five cases (20%), none in three cases (12%).

The therapy was found to be always well tolerated, no side effects having been observed.

By way of example certain treated cases are described hereafter.

1. G.M., female, aged 62. Clinical pattern: lumbosacral arthrosis with frequent painful acute aggravations; the patient had already been repeatedly treated in the past with various antiinflammatory agents and by a physical therapy.

Upon a painful aggravation with a highly algogenic symptomatology of the lumbosciatalgic type a treatment with (I) by 100 mg three times daily, was started. The patient reports on the first day already a fair symptomatologic relief; improvement persists on the second day with an increased possibility for movement and gait. On the third day the painful pattern has almost totally regressed.

The therapy was exceedingly well tolerated, no side effects having been observed.

2. N.M., female, aged 71. Clinical pattern: polyarthrosis and diffused rheumatalgia. The painful symptomatology is particularly relevant at the right knee which appears swollen, is painful on palpation and passive mobilization and is held in semiflexion in the antalgic position.

The compound (I) is administered, in the absence of any other antalgic-antiinflammatory treatment, during 8 days at a dosage of 100 mg three times daily. The patient reports a clear symptomatologic relief; gait is easier on the 4th and 5th day and mobility of the knee joint is improved.

Clearly positive clinical appreciation. No side effect.

3. P.M. female, aged 71. On a background of diffused osteoporosis, a pattern of cervical arthrosis with acute radiated pains at the nape and right brachialgia. Following an aggravation in the painful pattern, administration of (I) 100 mg three times daily, was started. The patient reports relief; disappearance of cephalgia, possibility of rotating the cervical column initially blocked by pain. Radiated pains at the shoulder and right arm persist, though of less intensity. The patient asks for continuation of the treatment, which is pursued during 7 days to almost total regression of algic aggravation. No side effect.

4. F.A., female, aged 54. Obese subject, with a radiologic pattern of bilateral coxo-arthrosis; the right coxa is very painful with a severe movements restriction. After treatment with Indomethacin had been stopped a few days, on reappearance of the painful pattern and functional impotence, compound (I) was administered by 100 mg, three times daily on the first and second days, 200 mg, three times daily on the third day. The result was a satisfactory response of the painful pattern with a progressive reduction in algic symptomatology; on the fifth day the patient can walk through still expressing a certain painfulness.

Appreciably favourable clinical response; no side effect.

5. M.C. male, aged 59. Screening discloses an arthrosic pattern of the spinal column, particularly accentuated at the cervical and lumbo-sacral levels. Painful symptomatology at the rachis with a radicular reaction. The compound (I) is administered by 100 mg, three times daily. The patient reports a good antalgic effect; improved freedom of active and passive movements of the spinal column.

The treatment is continued during 5 days without any side effect.

We claim:

1. A compound of the following structural formula

R — CH₂ — COX wherein R represents a group selected from:

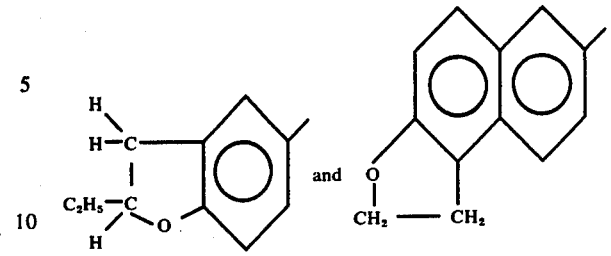

where:
X = OH, OCH₃, OC₂H₅; and their water soluble pharmaceutically acceptable salts.
2. 2,3-dihydro-2-ethyl-benzofuran-5-yl-acetic acid.
3. 1,2-dihydronaphtho [2,1-b]furan-7-yl-acetic acid.
4. An antiinflammatory formulation containing as active ingredient from 25 to 500 mg of at least one compound according to claim 1 in admixture with a pharmaceutically acceptable carrier.
5. A pharamaceutical formulation according to claim 4 for oral administration in the form of a tablet, capsule, dragee powder or syrup.
6. A pharmaceutical formulation according to claim 4 for rectal administration in the form of a suppository.
7. A pharmaceutical formulation according to claim 4 for parenteral administration.

* * * * *